United States Patent
Sudre et al.

(10) Patent No.: US 12,357,403 B2
(45) Date of Patent: Jul. 15, 2025

(54) ROBOT EQUIPPED WITH AN ULTRASOUND PROBE FOR REAL-TIME GUIDANCE IN PERCUTANEOUS INTERVENTIONS

(71) Applicant: Quantum Surgical, Montpellier (FR)

(72) Inventors: Mathieu Sudre, Restinclières (FR); Lucien Blondel, Montpellier (FR); Bertin Nahum, Castelnau-le-Lez (FR); Fernand Badano, Lyons (FR)

(73) Assignee: Quantum Surgical, Montpellier (FR)

( * ) Notice: Subject to any disclaimer, the term of this patent is extended or adjusted under 35 U.S.C. 154(b) by 38 days.

(21) Appl. No.: 18/571,438

(22) PCT Filed: Jun. 14, 2022

(86) PCT No.: PCT/FR2022/051137
§ 371 (c)(1),
(2) Date: Dec. 18, 2023

(87) PCT Pub. No.: WO2022/263764
PCT Pub. Date: Dec. 22, 2022

(65) Prior Publication Data
US 2024/0285355 A1 Aug. 29, 2024

(30) Foreign Application Priority Data
Jun. 16, 2021 (FR) ........................ 2106352

(51) Int. Cl.
*A61B 34/30* (2016.01)
*A61B 34/20* (2016.01)
*A61B 90/11* (2016.01)

(52) U.S. Cl.
CPC .............. *A61B 34/30* (2016.02); *A61B 90/11* (2016.02); *A61B 2034/2059* (2016.02)

(58) Field of Classification Search
CPC ......... A61B 34/30; A61B 34/20; A61B 34/10; A61B 34/25; A61B 2034/107;
(Continued)

(56) References Cited

U.S. PATENT DOCUMENTS

| 2017/0055940 A1* | 3/2017 | Shoham ................. A61B 90/11 |
| 2020/0281667 A1 | 9/2020 | Blondel et al. |

(Continued)

FOREIGN PATENT DOCUMENTS

| DE | 202018104487 U1 | 8/2018 |
| FR | 3103097 A1 | 5/2021 |
| WO | 2019136412 A1 | 7/2019 |

OTHER PUBLICATIONS

International Search Report in PCT/FR2022/051137, mailed Oct. 11, 2022, 8 pages.
(Continued)

*Primary Examiner* — Boniface N Nganga
(74) *Attorney, Agent, or Firm* — ArentFox Schiff LLP

(57) ABSTRACT

The invention relates to a medical robot comprising a robotic arm equipped with a tool guide for guiding a medical instrument along a trajectory defined by an entry point at the patient's skin and a target point at a lesion to be treated in an anatomical region of interest of the patient. The robotic arm is also provided with an ultrasound probe. The medical robot cooperates with a navigation system allowing determination of the position of a robot marker and the position of a patient marker. During a prepararatory phase, the robot is configured to place the ultrasound probe in contact with the patient and in a plane containing the lesion and the trajectory to be followed. During a guiding phase, the medical robot is configured to control the robotic arm in real
(Continued)

Figure 1:
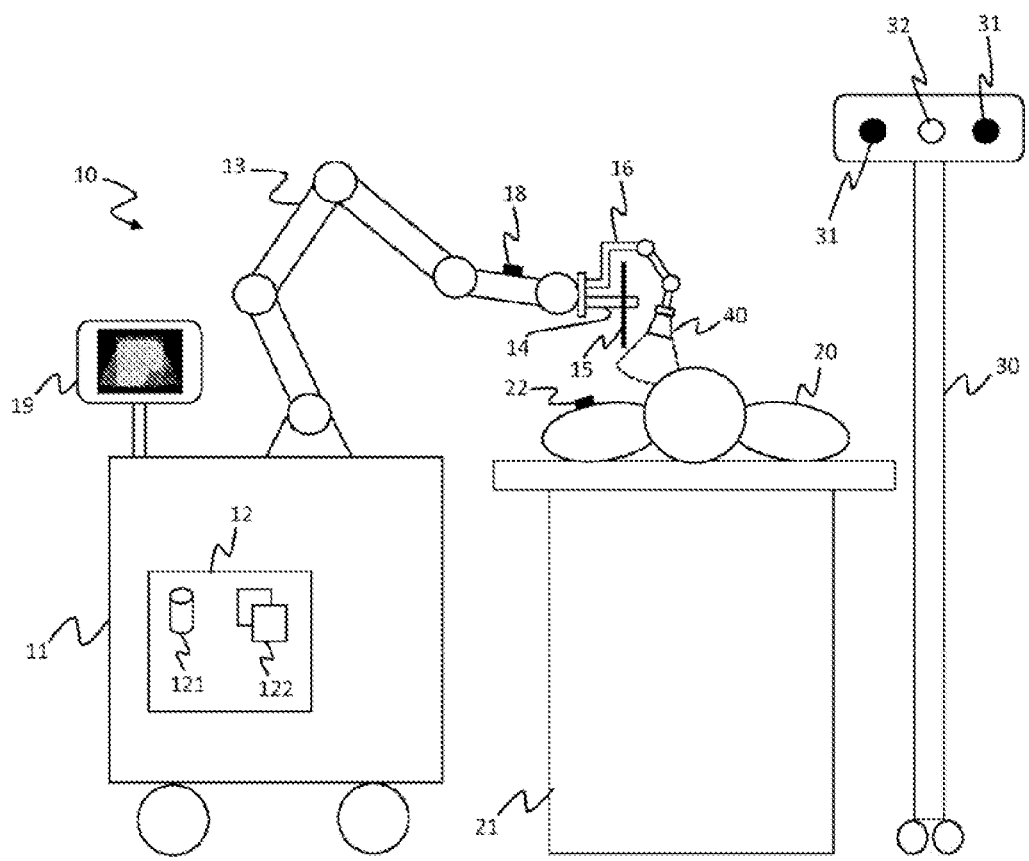

time based on the ultrasound images acquired by the ultrasound probe, in order to guide the medical instrument along the trajectory to be followed.

12 Claims, 5 Drawing Sheets

(58) Field of Classification Search
CPC .... A61B 2034/2055; A61B 2034/2059; A61B 90/11; A61B 2090/365; A61B 2090/378; A61B 2090/3966
See application file for complete search history.

(56) References Cited

U.S. PATENT DOCUMENTS

| | | |
|---|---|---|
| 2021/0113181 A1 | 4/2021 | Wu et al. |
| 2021/0161612 A1 | 6/2021 | Black et al. |

OTHER PUBLICATIONS

Written Opinion in PCT/FR2022/051137, mailed Oct. 11, 2022, 13 pages.

\* cited by examiner a)

b)

c)

ROBOT EQUIPPED WITH AN ULTRASOUND PROBE FOR REAL-TIME GUIDANCE IN PERCUTANEOUS INTERVENTIONS

CROSS-REFERENCE TO RELATED APPLICATIONS

This application is a National Phase of PCT/FR2022/051137, filed on Jun. 14, 2022, which claims priority to FR Patent Application No. FR2106352, filed on Jun. 16, 2021, the disclosures of which are hereby incorporated by reference in their entireties.

FIELD OF THE INVENTION

The methods and devices disclosed in the present application belong to the field of robotic devices for assisting a practitioner during a minimally invasive medical intervention comprising the insertion of one or more medical instruments into an anatomy of interest of a patient. In particular, the invention relates to a medical robot configured to track the movement of a target point in a lesion within a patient's anatomy of interest and to adjust in real time the position of an articulated arm of the robot in order to optimally guide a medical instrument to the target point. The movement of the target point may be generated in particular by the patient's breathing, or by the insertion of the medical instrument.

PRIOR ART

To prepare for a minimally invasive intervention aimed at reaching a target anatomical region in a patient's anatomy of interest using a medical instrument, a practitioner generally performs intervention planning based on a pre-operative medical image (obtained a few days or weeks before the intervention) or pre-interventional medical image (obtained just before the intervention, when the patient is on the intervention table). The minimally invasive medical intervention may be aimed in particular at performing the biopsy or ablation of a tumor in an organ, at performing a vertebroplasty or a cementoplasty, or even at stimulating a particular anatomical region. The anatomy of interest can be, for example, a lung, a kidney, the liver, the brain, a tibia, a knee, a vertebra, etc. The medical instrument may be a needle, a probe, a catheter, etc.

During this planning step, the practitioner defines a target point in a region of the anatomy of interest to be treated. The practitioner also defines an entry point for the medical instrument on the patient's skin. These two points then define a trajectory that the medical instrument must follow in order to carry out the medical intervention. In the particular case of the soft organs situated in the thoracic region, the abdominal region or the pelvic region, the movements linked to the patient's breathing and/or the local deformations of the organ due to the insertion of the medical instrument cause a displacement of the target point during the intervention. Pre-operative or pre-interventional medical planning images do not predict this movement of the target point during the intervention. Thus, the position of the target point (i.e. the position of the region to be treated in the anatomy of interest) is usually different during the acquisition of the medical planning image and during the intervention. Therefore, when the insertion of the medical instrument is planned from the medical planning image, there is a risk that the target point will not be reached with precision by the medical instrument.

In addition, there is a risk that the medical instrument will bend during insertion and will not reach the target point if the planned trajectory to be followed by the medical instrument is not adjusted accordingly.

In order to limit the movement of the target point generated by the patient's breathing, it is conceivable, at the time of insertion of the medical instrument, to block the patient's breathing at a phase of the respiratory cycle corresponding to that at which the medical planning image was acquired. Breathing may be blocked voluntarily by the patient if the medical intervention takes place under local anesthesia, or else in a controlled manner by the practitioner if the medical intervention takes place under general anesthesia (interruption of mechanical ventilation). However, this solution is not always very accurate because it is difficult to obtain an exact correspondence between the phase of the respiratory cycle at which the medical planning image was acquired and the phase of the respiratory cycle at which the patient's breathing is blocked during the intervention. Furthermore, this solution presupposes a relatively rapid insertion of the medical instrument, since this must be done while the patient's breathing is blocked.

It is also conceivable to take several medical planning images during a respiratory cycle of the patient and to determine the trajectory least subject to the deformations and movements of the anatomy of interest that are generated by respiration. However, there is again a risk that the target point will not be reached with precision by the medical instrument.

It is also conceivable to follow the position of the target point throughout the intervention by regularly acquiring intra-interventional medical images (images acquired when the medical instrument is inserted into the patient's body). These medical images are usually acquired by computed tomography, X-rays or magnetic resonance. In the case of computed tomography or X-rays, however, such a solution has the drawback of significantly irradiating the patient and the practitioner during the intervention. In the case of magnetic resonance imaging, it is necessary to use specific non-magnetic material, in particular for the anesthetic material, which is particularly restrictive. This solution also requires the use of bulky imaging devices throughout the intervention.

It is also known to follow the position of a lesion within an anatomy of interest with the aid of ultrasound images. However, the lesion is not always visible on an ultrasound image, and existing solutions generally lack precision.

It is still therefore necessary to find a solution for inserting a medical instrument accurately at a target point of a region to be treated within an anatomy of interest of a patient, in particular when the movements linked to the patient's breathing and/or the local deformations of the anatomy of interest due to the insertion of the medical instrument cause a displacement of the target point during the intervention.

DESCRIPTION OF THE INVENTION

The object of the methods and devices disclosed in the present application is to remedy all or some of the drawbacks of the prior art, in particular those set out above.

To this end, and according to a first aspect, in particular proposed is a medical robot for assisting a practitioner during a medical intervention to treat a lesion in an anatomy of interest of a patient. The medical robot comprises a robotic arm to which there are attached, at one end, an ultrasound probe and a tool guide for guiding a medical instrument. The medical robot also comprises a control unit configured to control the robotic arm. The medical robot is configured to cooperate with a navigation system. The control unit is configured to be able to determine at any time, on the basis of information communicated by the navigation system, the position of a robot marker intended to be positioned on the medical robot, and the position of a patient marker intended to be positioned on the patient near the anatomy of interest. During a preparation phase, the control unit is configured to:

- receive a planning image on which the lesion is visible and at least one radiopaque element of the patient marker,
- determine, from the planning image, a target point at the lesion and an entry point at the patient's skin, the target point and the entry point thus defining a trajectory to be followed for the medical instrument,
- control the robotic arm, according to the position of the robot marker and the position of the patient marker, so as to place the ultrasound probe in contact with the patient and in a plane containing the lesion and the trajectory to be followed.

During a guidance phase, the control unit is configured to receive, in real time, ultrasound images acquired by the ultrasound probe and to control the robotic arm in real time, based on these ultrasound images, in order to place the tool guide in such a way as to guide the medical instrument along the trajectory to be followed.

In the present application, the term "position" must be understood in the broad sense as describing both the position and the orientation of an object in a three-dimensional frame of reference (the term "pose" is sometimes used in English-language literature). The marker positions (patient marker and robot marker) and also the position of the target point and the position of the entry point can be defined in a robot reference frame or in a navigation system reference frame. It should be noted that the reference frame of the robot can be defined relative to the reference frame of the navigation system because the position of the robot marker is known both in the reference frame of the navigation system and in the reference frame of the robot (each articulation of the robotic arm comprises, for example, an encoder making it possible to know the position of each articulated element of the robotic arm in the reference frame of the robot, and the position of the robot marker on the robot is known a priori by the control unit).

For example, the planning image is a pre-interventional medical image acquired just before the intervention when the patient is on the intervention table, at a time when the patient marker is positioned on the patient near the anatomy of interest. The planning image can also be a pre-operative medical image acquired a few days or weeks before the intervention and registered with a pre-interventional image. The planning image is, for example, a medical image obtained by computed tomography, positron emission tomography or magnetic resonance imaging. The position of the patient marker can be determined on the planning image using the radiopaque marker of the patient marker that is visible on the planning image.

The target point and the entry point can be determined on the planning image by a segmentation artificial intelligence algorithm. In another example, the target point and the entry point can be determined on the planning image by the practitioner.

The target point and the entry point that are initially defined by the practitioner on the planning image can then be followed during the guidance phase on the ultrasound images acquired by the ultrasound probe (for example by a speckle deformation tracking algorithm) (the speckle represents the set of small, rapidly fluctuating spots that appear in the instant texture of an image and that give the latter a grainy appearance).

It is thus possible to track the position of the target point and the position of the entry point in real time from the ultrasound images. The robotic arm can then be moved in real time so that it is permanently positioned in such a way that the medical instrument is guided along the trajectory defined by the position of the target point and the position of the entry point. This real-time adjustment of the position of the robotic arm makes it possible to compensate for the movement of the target point generated by the patient's breathing. This real-time monitoring may in particular take place during a guidance phase of the tool guide, just before the insertion of the medical instrument.

With such arrangements, it becomes possible to block the patient's breathing at any instant of the respiratory cycle in order to proceed with the insertion of the medical instrument. Indeed, irrespective of the instant at which the patient's breathing is blocked, the robotic arm will be correctly positioned in order to allow the insertion of the medical instrument along the desired trajectory.

Moreover, it is no longer necessary to block the patient's breathing during the intervention. Indeed, the robotic arm is moved in real time so that the position of the robotic arm is constantly adjusted in order to guide the medical instrument along the desired trajectory.

The invention also makes it possible to minimize lateral readjustments of the trajectory after insertion of the medical instrument (such lateral readjustments of the trajectory are generally traumatic for the organ traversed by the medical instrument).

The medical instrument can thus be inserted with very great precision at the region to be treated, irrespective of the instant at which the medical instrument is inserted during the respiratory cycle. The insertion of the medical instrument is generally carried out by the practitioner, the object of the medical robot being to guide the insertion of the medical instrument by the practitioner. However, nothing would prevent the insertion of the medical instrument from being automated and controlled by the control unit.

Furthermore, since the real-time determination of the position of the target point and of the position of the entry point during the intervention is carried out on the basis of ultrasound images, the patient and the practitioner are not exposed to ionizing radiation during the intervention.

As soon as the medical instrument begins to be inserted into the patient's body, the position of the entry point at the patient's skin is fixed and becomes a pivot of rotation for the movements of the robotic arm. However, it is still possible to follow in real time the position of the target point and the position of the entry point from new ultrasound images acquired in real time during the insertion of the medical instrument.

Such arrangements make it possible to take into account any movement of the target point resulting from the insertion of the medical instrument. The target point can in fact move in the direction of the trajectory followed by the medical instrument during its insertion (this is particularly the case when the target point to be reached is in a lesion, for example a tumor, within a soft organ). The real-time determination of the position of the target point with the aid of the ultrasound images makes it possible to update in real time the trajectory to be followed by the medical instrument, and also the position of the robotic arm in order to guide the medical instrument along this trajectory.

In particular embodiments, the invention may further comprise one or more of the following features, taken in isolation or according to all technically possible combinations.

In particular embodiments, during the guidance phase, the control unit is configured, for each received ultrasound image, to:
generate a fusion image resulting from a registration of the ultrasound image with the planning image,
determine the position of the target point and the position of the entry point from the fusion image,
move the robotic arm so that the medical instrument is guided by the tool guide along the trajectory defined by the position of the target point and the position of the entry point.

The result of registering an ultrasound image with the planning image produces a fusion image on which the lesion is visible. The target point and entry point that are initially determined on the planning image can then also be identified on the fusion image.

In particular embodiments, during the guidance phase, during insertion of the medical instrument, and for each new ultrasound image received, the control unit is configured to determine the position of the medical instrument and to adjust the real-time control of the robotic arm based on the position of the medical instrument.

Such arrangements make it possible to keep the ultrasound probe in contact with the patient's body with adequate pressure during the patient's respiratory movements.

In particular embodiments, the ultrasound probe is coupled to a force sensor that enables the control unit to determine a pressure exerted on the patient's body by the ultrasound probe. The control unit is further configured to move the robotic arm so that the ultrasound probe exerts a predetermined pressure on the patient's body.

Such arrangements make it possible to take into account the risk of the medical instrument bending during insertion and to adjust the real-time control of the robotic arm accordingly (the trajectory to be followed by the medical instrument is then no longer a straight line between the entry point and the target point).

In particular embodiments, the planning image is a computed tomography image, a positron emission tomography image or a magnetic resonance imaging image.

In particular embodiments, in order to determine a target point and an entry point from the planning image, the control unit is configured to segment, on the planning image, the lesion and/or anatomical areas to be avoided using an artificial intelligence algorithm.

In particular embodiments, the ultrasound images received from the ultrasound probe are B-mode ultrasound images.

In particular embodiments, the control unit is configured to receive and process ultrasound images acquired by the ultrasound probe at a rate of at least fifteen images per second.

Such arrangements make it possible to guarantee real-time monitoring of the position of the target point and consequently real-time adjustment of the position of the robotic arm so that the medical instrument is guided along the desired trajectory throughout the intervention.

In particular embodiments, the medical robot further comprises a user interface comprising a display screen enabling the practitioner to view the planning image and/or fusion images.

In particular embodiments, the user interface comprises input means enabling the practitioner, during the preparation phase, to identify, on the planning image displayed on the display screen, a target point and/or an entry point and/or an anatomical area that is not to be traversed by the medical instrument.

In particular embodiments, the user interface comprises an augmented reality device for superimposing the analysis images with actual images of the patient's body on the display screen.

The augmented reality device makes it possible to superimpose on the patient's body the moving and three-dimensional lesion, and also the progression of the medical instrument during its insertion. It may be, for example, a screen positioned on the intervention table above the patient, or else a mask, a helmet or augmented reality glasses. This type of display facilitates the spatial representation of the anatomy of interest of the patient by the practitioner.

In particular embodiments, the control unit is further configured to compare an ultrasound image with the planning image and to determine a direction in which to move the ultrasound probe so that an ultrasound image acquired by the ultrasound probe comprises an anatomical region in which the lesion is located.

OVERVIEW OF THE FIGURES

Figure 2:
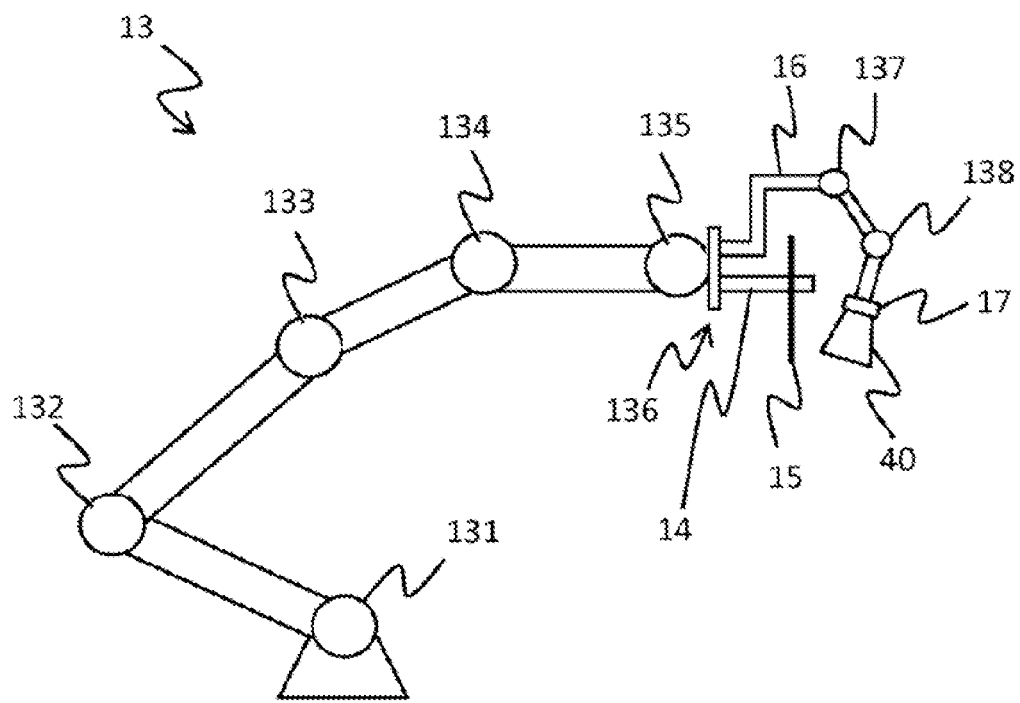
Figure 3:
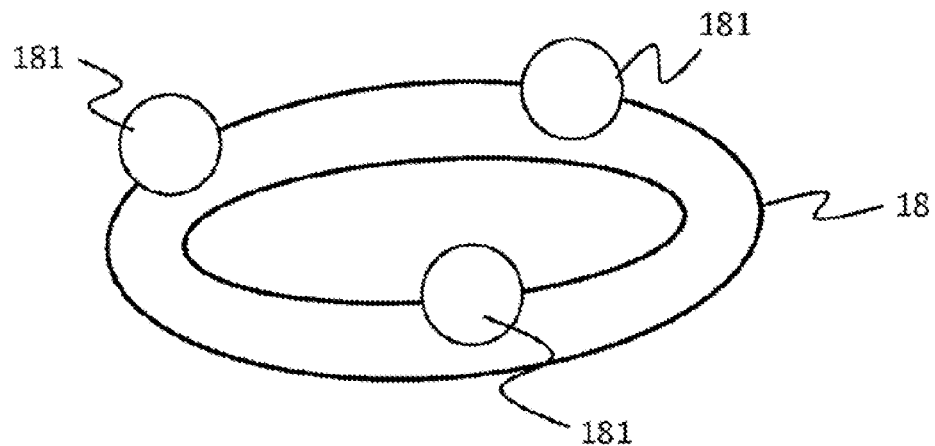
Figure 4:
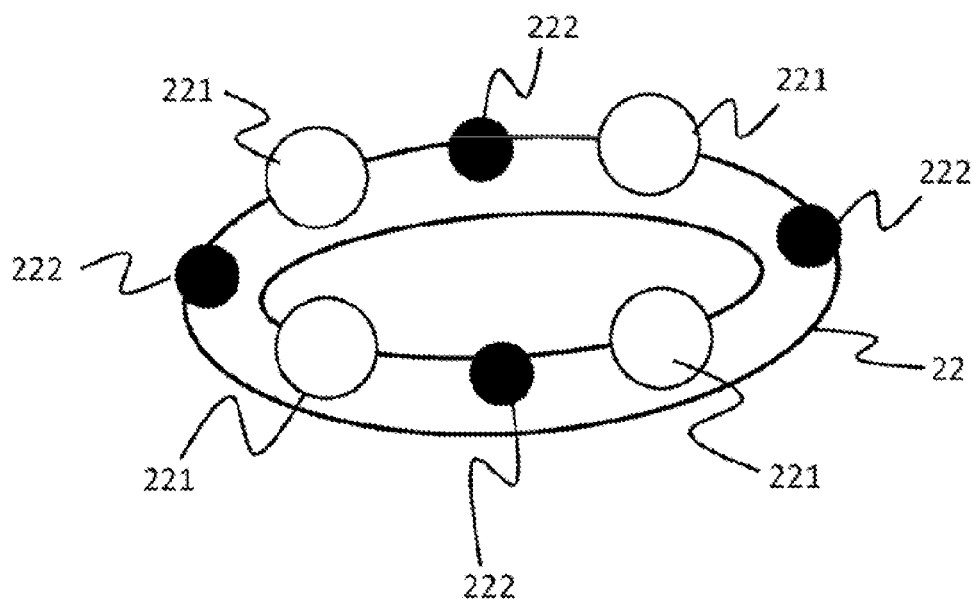
Figure 5:
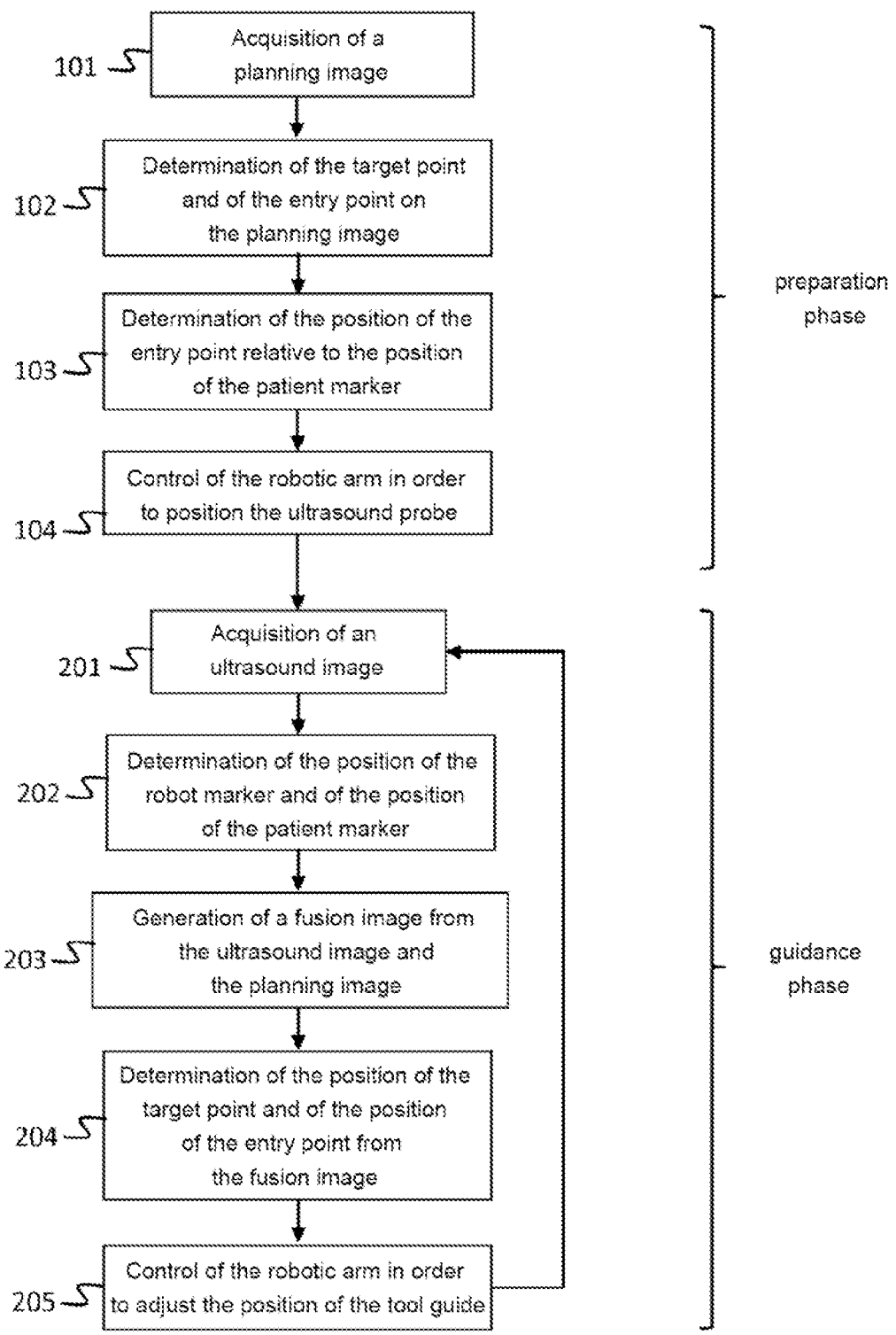
Figure 6:
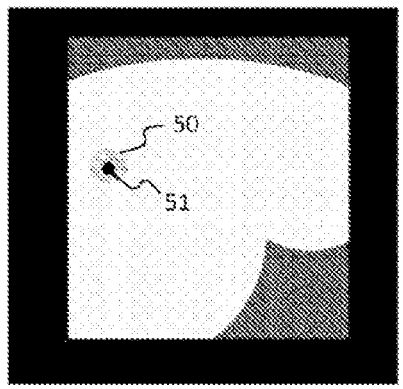
Figure 6:
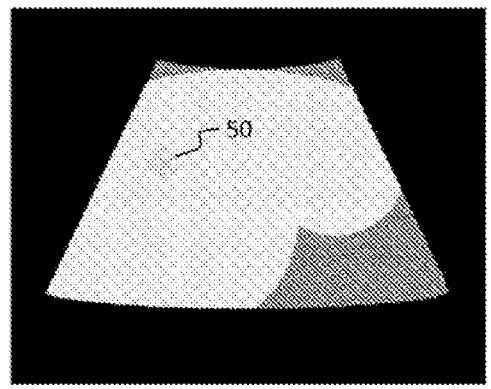
Figure 6:
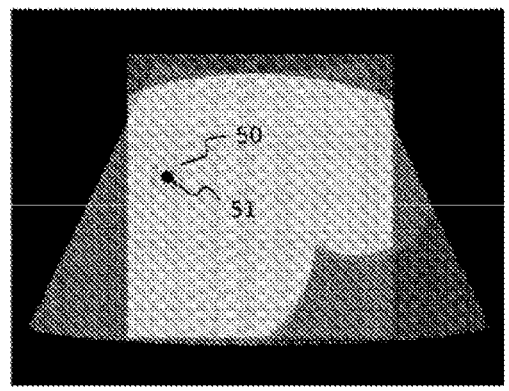

The invention will be better understood on reading the following description, given by way of non-limiting example and made with reference to FIGS. 1 to 6 which show:

FIG. 1 a schematic representation of a medical device comprising a medical robot according to the invention and a navigation system, FIG. 2 a schematic representation of the robotic arm of the medical robot, FIG. 3 a schematic representation of a "robot marker" intended to be attached to the medical robot, FIG. 4 a schematic representation of a "patient marker" intended to be positioned on the patient near the anatomy of interest, FIG. 5 a schematic representation of steps implemented by the control unit during a preparation phase and then during a real-time guidance phase of the robotic arm, FIG. 6 a schematic representation of a planning image (part a) of the figure), an ultrasound image (part b) of the figure), and a fusion image resulting from registration of the planning image and of the ultrasound image (part c) of the figure).

In these figures, identical references from one figure to another denote identical or analogous elements. For reasons of clarity, the elements represented are not necessarily on the same scale, unless otherwise stated.

DETAILED DESCRIPTION OF AN EMBODIMENT OF THE INVENTION

FIG. 1 shows schematically a medical robot 10 according to the invention. The medical robot 10 is used to assist a practitioner during a medical intervention on an anatomy of interest of a patient 20 positioned on an intervention table 21.

An example is the case of a medical intervention performed minimally invasively or percutaneously in order to treat a lesion within the anatomy of interest of the patient. This type of intervention generally requires the insertion by the practitioner of one or more medical instruments (for example a needle, a probe, a catheter, etc.) into the patient's body to a certain depth in order to reach a target anatomical region (a lesion, for example a tumor) in the anatomy of interest (for example in the liver, a lung, a kidney, etc.).

The medical robot 10 comprises a base 11. In the example considered, the base 11 of the medical robot 10 is equipped with motorized wheels, which allow the medical robot 10 to move in different directions by translational and/or rotational movements.

The medical robot 10 further comprises an articulated robotic arm 13, one end of which is connected to the base 11. Attached to the other end of the robotic arm 13 are an ultrasound probe 40 and a tool guide 14 intended to guide a medical instrument 15, for example a needle, a probe, a catheter, an electrode, etc.

In the example considered and illustrated in FIG. 1, the ultrasound probe 40 is attached to the robotic arm 13 via an additional arm 16. The additional arm 16 is also articulated so as to allow at least one additional degree of freedom for the ultrasound probe 40 with respect to the tool guide 14.

The medical robot 10 comprises a control unit 12 configured to control the movement of the robotic arm 13. In the present application, it is considered that the control of the robotic arm 13 also includes the control of the additional arm 16. The control unit 12 comprises one or more processors 122 and a memory 121 (magnetic hard disk, electronic memory, optical disk, etc.) in which a computer program product is stored, in the form of a set of program code instructions to be executed in order to implement the various steps of a method of positioning the robotic arm 13. The memory 121 also makes it possible to record the images and other information (in particular the navigation information) used to implement this method.

The medical robot 10 can then be used to assist a practitioner in positioning, holding and guiding the medical instrument 15 during the medical intervention. In a variant, the insertion of the medical instrument 15 can be fully automated and controlled by the control unit 12 of the medical robot 10. In addition, the medical robot 10 is used to automatically position the ultrasound probe 40.

The medical robot 10 can also comprise a user interface 19 comprising a display screen enabling the practitioner to view medical images (for example a planning image and/or ultrasound images acquired by the ultrasound probe 40 and fused with the planning image). The user interface can also comprise input means (keyboard, mouse, touch screen, etc.) enabling the practitioner to identify, on a planning image displayed on the display screen, a target point and/or an entry point and/or an anatomical area that is not to be traversed by the medical instrument 15.

In particular embodiments, the user interface can comprise an augmented reality device for superimposing the fused images with actual images of the patient's body on the display screen. Such a device facilitates the spatial representation of the anatomy of interest for the practitioner.

The medical robot 10 is configured to cooperate with a navigation system 30. The medical robot 10 comprises a communication module connected to the control unit 12 for exchanging data with the navigation system 30. The navigation system 30 also comprises a communication module for exchanging data with the control unit 12 of the medical robot 10. The communications established between the control unit 12 and the navigation system 30 may be wired communications or wireless communications. For the sake of simplification, the communication modules are not shown in FIG. 1.

In the example considered, the navigation system 30 is an optical navigation system. The navigation system 30 comprises two optical sensors 31 corresponding to two sensors of a stereoscopic camera operating in the infrared radiation range. In the example considered, the navigation system 30 further comprises a camera 32 operating in the visible light range.

The control unit 12 is configured to be able to determine at any time, from information communicated by the navigation system 30, the position of a robot marker 18 to be attached to the medical robot 10 and the position of a patient marker 22 to be positioned on the patient 20 near the anatomy of interest.

In the present application, the term "position" corresponds to the combination of the position and the orientation of an object in a given frame of reference which is generally a three-dimensional coordinate system. The term "pose" is used in the English-language literature to represent this combination of the position and orientation of an object in space.

The control unit 12 is configured to receive ultrasound images acquired by the ultrasound probe 40.

The ultrasound images received from the ultrasound probe 40 and the information received from the navigation system 30 are synchronized in time by the control unit 12 so as to be able to correlate the position of the lesion with the position of the patient marker 22 at a given instant.

Conventionally, the ultrasound probe 40 comprises one or more sound wave transmitter-receiver elements (piezoelectric materials, capacitive electronic transducers). The ultrasound probe produces ultrasonic waves by an indirect piezoelectric effect. Each time a wave encounters an anatomical structure, a part of this wave returns by reflection or scattering ("speckle") in the form of an echo. This echo is then transformed into electric current by a direct piezoelectric effect and then reconstructed into an image. The reconstruction of an ultrasound image depends mainly on the number, size and positions of the transmitter-receiver elements of the probe (lateral and longitudinal resolution), the duration of the emission pulses and the echo times (axial and/or depth resolution). The energy of the received echo is then coded in gray level. The higher the energy, the whiter the corresponding image portion (pixel). This grayscale encoding is called "brightness", and the associated ultrasound mode is called "B-mode". The images produced by the ultrasound probe 40 may be two-dimensional images or three-dimensional images. Preferably, the ultrasound probe 40 is capable of generating images at a rate of at least fifteen images per second.

The B-mode is particularly suitable when the anatomy of interest is the liver. It should however be noted that the invention could also be applied with other ultrasound modes, for example elastography.

In the example considered, and as illustrated in FIG. 2, the robotic arm 13 comprises six rotoid articulations 131 to 136 conferring six degrees of freedom, making it possible to place the medical instrument 15 in any position of the three-dimensional space. Advantageously, the articulations 131 to 135 of the robotic arm 13 are not aligned and are offset with respect to one another, which allows a greater number of possible configurations of the robotic arm 13. The rotoid articulation 136 corresponds to a rotation about an axis parallel to the main axis of the tool guide 14.

In the example considered, the ultrasound probe 40 is attached to the robotic arm 13 via an additional arm 16 comprising two rotoid articulations 137 and 138, conferring two additional degrees of freedom for the movement of the ultrasound probe 40 with respect to the tool guide 14. However, it should be noted that the reverse is also possible: the ultrasound probe 40 could be attached directly to the distal end of the robotic arm 13, and an additional arm could carry the tool guide 14. The tool guide 14 and the additional arm 16 are attached to the end of the robotic arm 13 by means of a clamp. In the example considered and illustrated in FIG. 2, the ultrasound probe 40 is also coupled to a force sensor 17 enabling the control unit 12 to determine a force exerted on the ultrasound probe 40 by the patient's body 20.

The additional arm 16 and the tool guide 14 are arranged with respect to each other in such a way that the medical instrument 15 is always in the plane of an ultrasound image acquired by the ultrasound probe 40.

Each articulation 131 to 138 comprises at least one encoder making it possible to know its angular position in real time. A configuration of the robotic arm 13 then corresponds to a set of parameter values taken by the articulations 131 to 138 (for example the value of an angle of rotation for each articulation).

FIG. 3 diagrammatically shows the robot marker 18 intended to be positioned on the medical robot 10. In the example considered, the robot marker comprises three optical markers 181, so that the position of the robot marker 18 can be determined in the three spatial dimensions of the reference frame of the navigation system 30. The respective positions of the optical markers 181 of the robot marker 18 relative to one another are known a priori by the navigation system 30 and/or by the control unit 12. Advantageously, the geometric shape of each optical marker 181 can also be known a priori. In the example shown in FIG. 3, the optical markers 181 are spherical in shape. The spherical shape makes it possible to optimize the reflection of the optical radiation.

The use of at least three optical markers 181 makes it possible to define a plane and therefore a direct orthonormal three-dimensional reference frame with a z axis normal to the plane and x and y axes in the plane, so that the reference frame is direct. This thus makes it possible to determine the position and orientation of the reference frame formed from the optical markers 181. The three axes x, y and z make it possible to define six degrees of freedom, namely a translation along each of the axes x, y or z and a rotation about each of these axes.

The optical markers 181 may be passive or active. Passive optical markers reflect optical radiation emitted by another element, such as for example the navigation system 30. Passive optical markers may correspond, for example, to reflecting spheres detectable by an infrared stereoscopic camera (this is what is used, for example, in the Polaris® navigation systems manufactured by Northern Digital Inc.), or to black and white patterns visible by a stereoscopic camera (this is what is used, for example, in the MicronTracker® navigation system from ClaroNav). Active optical markers themselves emit optical radiation, for example infrared radiation, detectable by the navigation system 30.

However, it should be noted that a single optical marker having a three-dimensional characteristic geometric shape could be used instead of the set of spherical optical markers 181.

FIG. 4 schematically shows the patient marker 22 intended to be positioned on the patient 20 near the anatomy of interest. The patient marker 22 comprises at least three optical markers 221 (it contains four in the example illustrated in FIG. 4), so that the position of the patient marker 22 can be determined in the three spatial dimensions of the reference frame of the navigation system 30. The respective positions of the optical markers 221 of the patient marker 22 relative to one another are known a priori by the navigation system 30 and/or by the control unit 12. Advantageously, the geometric shape of each optical marker 221 can also be known a priori. In the example illustrated in FIG. 4, the optical markers 221 are spherical in shape. The spherical shape makes it possible to optimize the reflection of the optical radiation. What was mentioned above for the active or passive type of the optical markers 181 of the tool guide 14 is also true for the optical markers 221 of the patient reference 22. Here again, it would be possible to envision using a single optical marker having a characteristic geometric shape in three dimensions instead of the set of spherical optical markers 221.

The patient marker 22 also comprises radiopaque markers 222 that are visible on a medical image acquired by a medical imaging device (for example by computed tomography, by magnetic resonance, by ultrasound, by tomography, by positron emission, etc.). The respective positions of the radiopaque markers 222 relative to one another are known a priori by the navigation system 30 and/or by the control unit 12. Advantageously, the geometric shape of the radiopaque markers 222 can also be known a priori. Preferably, the patient marker 22 comprises at least three radiopaque markers 222 (in the example considered, the patient marker 22 comprises four radiopaque markers 222). The radiopaque markers 222 may be ceramic beads, for example. It should be noted, however, that a single radiopaque marker having a characteristic three-dimensional geometric shape could be used instead of the set of spherical radiopaque markers 222.

In the remainder of the description, it is considered by way of non-limiting example that the optical sensors 31 of the navigation system 30 and the various optical markers 181, 221 are designed to operate with infrared type optical radiation. It is also considered that the optical markers 181, 221 are passive markers. The optical sensors 31 are configured to emit infrared radiation. This infrared radiation is reflected by the various optical markers 181, 221 toward the optical sensors 31. The optical sensors 31 are configured to receive this reflected infrared radiation. The navigation system 30 can then determine the distance between an optical marker 181, 221 and an optical sensor 31 by measuring the time taken by an infrared ray to make the round trip between said optical sensor 31 and said optical marker 181, 221. By knowing the distance between each optical marker 181, 221 and each optical sensor 31, and by knowing a priori the arrangement of the optical markers 181, 221 with respect to one another on the robot marker 18 and on the patient marker 22, it is possible to determine the position of the robot marker 18 and the position of the patient marker 22 in the reference frame of the navigation system 30.

It should be noted that the invention is described using an optical navigation system. However, nothing would prevent the use, in a variant, of an electromagnetic navigation system in place of the optical navigation system. In this case, the various "markers" detectable by the navigation system (patient marker 22, robot marker 18) would then correspond to electromagnetic sensors whose position can be determined by the navigation system in a generated electromagnetic field.

In the example considered, the control unit 12 of the medical robot 10 is configured to receive from the navigation system 30 information on the current position of the robot marker 18 in the reference frame of the navigation system 30. Now, the control unit 12 of the medical robot 10 knows the current position of the robot marker 18 in the reference frame of the medical robot 10 (via the encoders of the articulations 131 to 138). The control unit 12 can therefore determine the transformation to be carried out in order to define a position in the reference frame of the medical robot 10 from a position in the reference frame of the navigation system 30.

It is also possible to deduce the position of the ultrasound probe 40 and the position of the tool guide 14 from the position of the robot marker 18 (via the encoders of the articulations 131 to 138).

The control unit 12 is also configured to receive from the navigation system 30 information on the position of the patient marker 22 in the reference frame of the navigation system 30. The control unit 10 can then define the position of the patient marker 22 in the reference frame of the medical robot 10.

The position of an entry point of the medical instrument 15 at the patient's skin and the position of a target point at the lesion to be treated can be determined relative to the position of the patient marker 22 on a medical planning image on which are visible both the lesion and the radiopaque elements 222 of the patient marker 22. When the position of the patient marker 22 is known in the reference frame of the navigation system or in the reference frame of the medical robot 10, it then becomes possible to deduce therefrom the position of the entry point and the position of the target point in the reference frame of the navigation system or in the reference frame of the medical robot 10.

When the position of the ultrasound probe 40 is known at a given time, it is possible to determine the position of a visible element on an ultrasound image acquired by the ultrasound probe 40 at that time. This visible element can correspond in particular to the target point or the entry point. The target point and the entry point define a trajectory to be followed by the medical instrument 15. When the position of the target point and the position of the entry point are known, i.e. when the trajectory to be followed by the medical instrument 15 is defined, the control unit can automatically move the robotic arm 13 into a configuration that allows the tool guide 14 to guide the medical instrument 15 along the defined trajectory.

The movements related to the patient's breathing cause a displacement of the target point and of the entry point in the reference frame of the medical robot 10. Thus, the trajectory to be followed by the medical instrument 15 at a given instant of the patient's respiratory cycle is not the same at another instant of the respiratory cycle. The position of the target point and the position of the entry point must therefore be monitored in real time in order to be able at any moment to determine the trajectory to be followed by the medical instrument 15 and to adjust the position of the tool guide 14 so that it guides the medical instrument 15 according to this trajectory.

FIG. 5 shows, by way of example, steps that are implemented by the control unit 12 in order to enable this real-time monitoring. These steps may in particular take place before the insertion of the medical instrument 15. In a first step, a preparation phase consists mainly in placing the ultrasound probe 40 at a suitable position in order to acquire ultrasound images of the lesion. In a second step, a guidance phase consists in controlling the robotic arm 13 on the basis of the ultrasound images acquired by the ultrasound probe 40 in order to adjust in real time the position of the tool guide 14, in such a way that the medical instrument 15 is constantly positioned along the trajectory to be followed.

The preparation phase comprises a step of receiving 101 a planning image on which the lesion is visible and at least one radiopaque element 222 of the patient marker 22. The planning image is, for example, a pre-interventional medical image acquired just before the intervention when the patient 20 is on the intervention table, at a time when the patient marker 22 is positioned on the patient 20 near the anatomy of interest. The planning image can also be a pre-operative medical image acquired a few days or weeks before the intervention and registered with a pre-interventional image. The planning image is, for example, a medical image obtained by computed tomography, positron emission tomography or magnetic resonance imaging. The position of the patient marker 22 can be determined on the planning image using the radiopaque marker 222 of the patient marker 22 that is visible on the planning image.

The preparation phase then comprises a step of determining 102 a target point and an entry point on the planning image. According to a first example, the planning image is displayed on a screen of the user interface 19, and the user interface 19 enables the practitioner to identify on the planning image a target point at the region to be treated, and/or an entry point at the patient's skin, and/or a risk area to be avoided (for example the bones or blood vessels), and treatment parameters. This step can be facilitated by segmentation of certain anatomical regions (anatomy of interest, lesion to be treated, risk areas, etc.) by a machine learning algorithm. In another example, the target point and the entry point can be directly determined on the planning image by an artificial intelligence algorithm.

The preparation phase then comprises a step of determining 103 the position of the target point and the position of the entry point relative to the position of the patient marker 22. The position of the patient marker 22 can in fact be determined on the planning image using the radiopaque elements 222 that are visible on the planning image. Furthermore, by virtue of the navigation system 30, the position of the patient marker 22 can be determined at any time in the reference frame of the navigation system 30 or in the reference frame of the medical robot 10. It is therefore possible to deduce therefrom the position of the entry point and the position of the target point in the reference frame of the navigation system or in the reference frame of the medical robot 10.

Finally, the preparation phase comprises a step of real-time control of the robotic arm 13 in order to position the ultrasound probe 40 so that it is in contact with the patient 20 and so that an ultrasound image acquired by the ultrasound probe 40 at this position is in a plane containing the lesion and the trajectory to be followed by the medical instrument 15. As a reminder, the tool guide 14 and the ultrasound probe 40 are arranged relative to each other in such a way that the medical instrument 15 is always in the plane of an ultrasound image acquired by the ultrasound probe 40. The real-time control of the robotic arm 13 includes the control of the additional arm 16 to which the ultrasound probe 40 is attached.

In the example considered, the force sensor 17 enables the control unit 13 to determine a pressure exerted on the body of the patient 20 by the ultrasound probe 40. The control unit 12 is configured to move the robotic arm 13 so that the ultrasound probe 40 exerts a predetermined pressure on the body of the patient 20. Such arrangements make it possible to keep the ultrasound probe 40 in contact with the body of the patient 20 during the respiratory movements of the patient 20. When a respiratory movement of the patient 20 induces too great a pressure of the ultrasound probe 40 on the body of the patient 20 (inhalation), then the ultrasound probe 40 is moved in a direction away from the body of the patient 20. By contrast, when a respiratory movement of the patient 20 induces too low a pressure of the ultrasound probe 40 on the body of the patient 20 (exhalation), then the ultrasound probe is moved toward the body of the patient 20.

The target point and the entry point that are initially defined by the practitioner on the planning image can then be monitored during the guidance phase on ultrasound images that are acquired in real time by the ultrasound probe.

The monitoring of the target point can be implemented in particular by a method of tracking movement in several successive images, by an analysis of deformation of the speckle or by an artificial intelligence algorithm. When the lesion is not visible on the ultrasound image, in order to assist in tracking the target point on the fusion images, it may be advantageous to track the movement of an anatomical structure close to the lesion visible on the ultrasound images (for example a blood vessel). However, the chosen anatomical structure must be visible in the plane of an ultrasound image acquired by the ultrasound probe.

If the lesion is not sufficiently visible on the ultrasound images, the movement of the target point should be tracked on fusion images, each fusion image corresponding to a registration of the ultrasound image with the planning image.

The guidance phase comprises a step of receiving 201 an ultrasound image acquired by the ultrasound probe 40.

The guidance phase comprises a step of determining 202 the position of the robot marker 18 and the position of the patient marker 22 at the instant at which the ultrasound image was acquired by the ultrasound probe 40.

The guidance phase then comprises a step of generating 203 a fusion image resulting from a registration of the ultrasound image with the planning image. The lesion, the target point and the entry point are therefore visible on the fusion image obtained.

FIG. 6 schematically illustrates a planning image (part a) of FIG. 6) for registering an ultrasound image (part b) of FIG. 6) in order to form a fusion image (part c) of FIG. 6) resulting from the registration of the planning image with the ultrasound image. The lesion to be treated 50 and the target point 51 are visible on the planning image. In the example considered, the reference image is acquired by computed tomography. On the other hand, the lesion to be treated 50 is barely visible on the ultrasound image. The lesion to be treated 50 and the target point 51 become visible on the analysis image resulting from the registration of the reference image with the ultrasound image. It should be noted that (although not shown in FIG. 6) the radiopaque markers 222 of the patient marker 22 are also visible on the planning image and on the fusion image.

The registration can be global (registration on the entire anatomy of interest) or local (optimized registration on a particular region of the anatomy of interest). The registration can be done rigidly (by translation and/or rotation) or non-rigidly (with deformation). The registration can in particular be implemented by a machine learning algorithm based on the recognition of particular anatomical structures on the images to be merged. The registration can also be based on segmentation of the radiopaque element of the patient marker on the planning image and then registration between the reference frame of the planning image (known via the position of the patient marker 22) and the reference frame of the ultrasound image (known via the position of the robot marker 18).

The guidance phase then comprises a step of determining 204 the position of the target point and the position of the entry point from the fusion image, the position of the robot marker 18 and the position of the patient marker 22. The position of the target point and the position of the entry point can be defined relative to the position of the patient marker 22 in a reference frame of the fusion image. Knowing the position of the patient marker 22 and the position of the robot marker 18 then makes it possible to determine the position of the target point and the position of the entry point in the reference frame of the navigation system 30 and/or in the reference frame of the medical robot 10.

However, it should be noted that it is not essential to determine the position of the robot marker 18 and the position of the patient marker 22 for each new ultrasound image acquired by the ultrasound probe 40 (this means that step 202 is optional). Indeed, since the position of the ultrasound probe 40 is known in the reference frame of the medical robot 10, the reference frame of the fusion image can be defined with respect to the reference frame of the medical robot 10, and it is therefore possible to determine the position of the target point and the position of the entry point in the reference frame of the medical robot 10 directly from the fusion image.

The guidance phase then comprises a step of moving 205 the robotic arm 13 so that the medical instrument 15 is guided by the tool guide 14 along the trajectory defined by the position of the target point and the position of the entry point.

Steps 201 to 205 are repeated for each new ultrasound image received from the ultrasound probe 40.

The robotic arm is thus moved in real time so that it is permanently positioned in such a way that the medical instrument 15 is guided along the trajectory defined by the position of the target point and the position of the entry point. This real-time adjustment of the position of the robotic arm 13 makes it possible to compensate for the movement of the target point generated by the patient's breathing.

With such arrangements, it becomes possible to block the patient's breathing at any instant of the respiratory cycle in order to proceed with the insertion of the medical instrument 15. Indeed, irrespective of the instant at which the patient's breathing is blocked, the robotic arm 13 will be correctly positioned in order to allow the insertion of the medical instrument 15 along the desired trajectory.

Moreover, it is no longer necessary to block the patient's breathing during the intervention. Indeed, the robotic arm is moved in real time so that the position of the robotic arm is constantly adjusted in order to guide the medical instrument along the desired trajectory.

As soon as the medical instrument 15 begins to be inserted into the body of the patient 20, the position of the entry point at the patient's skin is fixed and becomes a pivot of rotation for the movements of the robotic arm 13. However, it remains possible to follow in real time the position of the target point and the position of the entry point from new ultrasound images acquired in real time during the insertion of the medical instrument 15. This makes it possible in particular to take into account any movement of the target point resulting from the insertion of the medical instrument 15. The target point can in fact move in the direction of the trajectory followed by the medical instrument 15 during its insertion (this is particularly the case when the lesion is located in soft tissues). The real-time determination of the position of the target point with the aid of the ultrasound images makes it possible to update in real time the trajectory to be followed by the medical instrument 15, and also the position of the robotic arm 13 in order to guide the medical instrument 15 along this trajectory.

It should be noted that the position of the ultrasound probe 40 can be adjusted during the guidance phase, depending on the position of the patient marker 22 and/or depending on the measurements reported by the force sensor 17, in order to remain in contact with the patient 20 and to remain in a plane containing the lesion and the trajectory to be followed by the medical instrument 15. The additional degrees of freedom provided by the additional arm 16 make it possible to adjust the position of the ultrasound probe 40 without impacting on the position of the tool guide 14.

During the preparation phase, if the lesion is not within the field of view of the ultrasound probe 40, i.e. if the lesion is not visible on an ultrasound image acquired by the ultrasound probe 40 (or by the associated fusion image), the ultrasound probe 40 must be moved so that the lesion is within the field of view of the ultrasound probe 40. For this purpose, the control unit 12 can be configured to compare an ultrasound image with the planning image (on which the lesion is visible) and to determine a direction in which to move the ultrasound probe 40 so that an ultrasound image acquired by the ultrasound probe 40 comprises an anatomical region in which the lesion is located. The control unit 12 can then control the robotic arm 13 to move the ultrasound probe 40 in this direction. Alternatively, the control unit 12 can control the robotic arm 13 to scan with the ultrasound probe 40 until the lesion is detected on an ultrasound image acquired by the ultrasound probe (or on the associated fusion image).

The invention claimed is:

1. A medical robot for assisting a practitioner during a medical intervention for treating a lesion in an anatomy of interest of a patient, said medical robot comprising a robotic arm to which are attached, at one end, an ultrasound probe and a tool guide for guiding a medical instrument, and a control unit configured to control the robotic arm, the medical robot being configured to cooperate with a navigation system, the control unit being configured to be able to determine at any time, on the basis of information communicated by the navigation system, the position of a robot marker intended to be positioned on the medical robot and the position of a patient marker intended to be positioned on the patient near the anatomy of interest, wherein
during a preparation phase, the control unit is configured to:
receive a planning image on which the lesion is visible and at least one radiopaque element of the patient marker,
determine, from the planning image, a target point at the lesion and an entry point at the skin of the patient, the target point and the entry point thus defining a trajectory to be followed for the medical instrument, and
control the robotic arm, according to the position of the robot marker and the position of the patient marker, so as to place the ultrasound probe in contact with the patient and in a plane containing the lesion and the trajectory to be followed, and
during a guidance phase, the control unit is configured to receive, in real time, ultrasound images acquired by the ultrasound probe and to control the robotic arm in real time, based on said ultrasound images, in order to place the tool guide in such a way as to guide the medical instrument along the trajectory to be followed.

2. The medical robot of claim 1, wherein, during the guidance phase, the control unit is configured, for each received ultrasound image, to:
generate a fusion image resulting from a registration of the ultrasound image with the planning image,
determine the position of the target point and the position of the entry point from the fusion image, and
move the robotic arm so that the medical instrument is guided by the tool guide along the trajectory defined by the position of the target point and the position of the entry point.

3. The medical robot of claim 1, wherein, during the guidance phase, during the insertion of the medical instrument, for each new ultrasound image received, the control unit is configured to determine the position of the medical instrument and to adjust the real-time control of the robotic arm based on the position of the medical instrument.

4. The medical robot of claim 1, wherein the ultrasound probe is coupled to a force sensor enabling the control unit to determine a pressure exerted on the body of the patient by the ultrasound probe, and the control unit is configured to move the robotic arm so that the ultrasound probe exerts a predetermined pressure on the body of the patient.

5. The medical robot of claim 1, wherein the planning image is a computed tomography image, a positron emission tomography image or a magnetic resonance imaging image.

6. The medical robot of claim 1, wherein, in order to determine a target point and an entry point from the planning image, the control unit is configured to segment, on the planning image, the lesion and/or anatomical areas to be avoided using an artificial intelligence algorithm.

7. The medical robot of claim 1, wherein the ultrasound images received from the ultrasound probe are B-mode ultrasound images.

8. The medical robot of claim 1, wherein the control unit is configured to receive and process ultrasound images acquired by the ultrasound probe at a rate of at least fifteen images per second.

9. The medical robot of claim 1, further comprising a user interface comprising a display screen enabling the practitioner to view the planning image and/or the fusion images.

10. The medical robot of claim 9, wherein the user interface comprises input means enabling the practitioner, during the preparation phase, to identify, on the planning image displayed on the display screen, a target point and/or an entry point and/or an anatomical area that is not to be traversed by the medical instrument.

11. The medical robot of claim 9, wherein the user interface comprises an augmented reality device for superimposing the analysis images with actual images of the patient's body on the display screen.

12. The medical robot of claim 1, wherein the control unit is further configured to compare an ultrasound image with the planning image, and to determine a direction in which to move the ultrasound probe so that an ultrasound image acquired by the ultrasound probe comprises an anatomical region in which the lesion is located.

* * * * *